United States Patent
Hatajima et al.

(10) Patent No.: US 7,199,101 B2
(45) Date of Patent: Apr. 3, 2007

(54) GELLING AGENT FOR OIL

(75) Inventors: Toshihiko Hatajima, Kawasaki (JP); Naoya Yamato, Kawasaki (JP); Tatsuya Hattori, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 10/987,726

(22) Filed: Nov. 12, 2004

(65) Prior Publication Data
US 2005/0100572 A1 May 12, 2005

(30) Foreign Application Priority Data
Nov. 12, 2003 (JP) .............................. 2003-382921

(51) Int. Cl.
| | |
|---|---|
| A61K 38/00 | (2006.01) |
| A61K 9/00 | (2006.01) |
| A61K 6/00 | (2006.01) |
| A61K 8/02 | (2006.01) |
| A61K 8/00 | (2006.01) |
| A61K 8/18 | (2006.01) |
| A61Q 15/00 | (2006.01) |
| A61K 8/28 | (2006.01) |
| A61K 8/58 | (2006.01) |
| A61K 8/27 | (2006.01) |
| A61K 8/26 | (2006.01) |

(52) U.S. Cl. .............................. 514/9; 514/10; 514/11; 514/844; 514/845; 514/846; 514/847; 514/848; 424/400; 424/401; 424/65; 424/66; 424/67; 424/68

(58) Field of Classification Search .............. 514/9–11, 514/844–848; 424/400, 401, 65–68
See application file for complete search history.

(56) References Cited

U.S. PATENT DOCUMENTS

| | | | |
|---|---|---|---|
| 3,969,087 | A | 7/1976 | Saito et al. |
| 5,591,424 | A | 1/1997 | Hofrichter et al. |
| 5,972,319 | A * | 10/1999 | Linn et al. .................. 424/65 |
| 2002/0159961 | A1 | 10/2002 | Yamato et al. |
| 2004/0223995 | A1 | 11/2004 | Emslie et al. |

FOREIGN PATENT DOCUMENTS

| | | |
|---|---|---|
| WO | WO 93/23008 A1 | 11/1993 |
| WO | WO 200042071 A2 * | 7/2000 |
| WO | WO 2004/105707 A1 | 12/2004 |

OTHER PUBLICATIONS

Rodehüser et al., Amino Acids, 18: 89-100 (2000).

* cited by examiner

Primary Examiner—Sreeni Padmanabhan
Assistant Examiner—Abigail M. Cotton
(74) Attorney, Agent, or Firm—Wenderoth, Lind & Ponack, LLP.

(57) ABSTRACT

A gelling agent for an oil, which contains at least one compound (A) and at least one compound (B), and a gel composition containing the gelling agent and an oil:

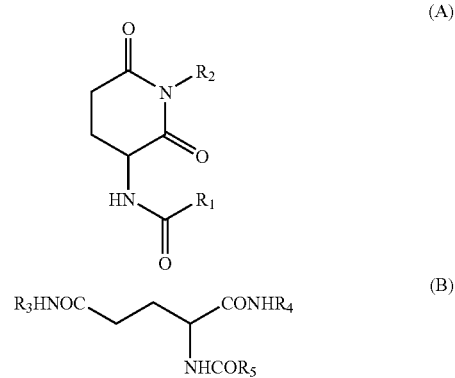

wherein $R_1$ is a straight chain or branched chain, saturated or unsaturated hydrocarbon group having 7 to 17 carbon atoms, $R_2$ is a straight chain or branched chain, saturated or unsaturated hydrocarbon group having 1 to 26 carbon atoms, $R_3$ and $R_4$ are each independently a straight chain or branched chain, saturated or unsaturated hydrocarbon group having 1 to 26 carbon atoms, and $R_5$ is a straight chain or branched chain, saturated or unsaturated hydrocarbon group having 7 to 17 carbon atoms.

23 Claims, No Drawings

GELLING AGENT FOR OIL

TECHNICAL FIELD OF THE INVENTION

The present invention relates to a gelling agent for an oil. More particularly, the present invention relates to a gelling agent for an oil, which contains a specific amino acid derivative. The gelling agent of the present invention is useful for providing various forms by gelling an oil which is a liquid at an ordinary temperature.

BACKGROUND OF THE INVENTION

Conventionally, as a gelling agent for a water insoluble oil, a polyamide resin, 12-hydroxystearic acid, condensates of an aromatic aldehyde and a polyhydric alcohol represented by dibenzylidene-D-sorbitol, and the like are generally known. However, these gelling agents are associated with a problem in that they have low solubility in oil. For example, gel compositions prepared using these gelling agents are problematic in that they show poor dissolution stability, become heterogeneous, and exhibit a sweating phenomenon wherein a gelatinized oil exudes out from the gel surface due to changes over time.

As a different gelling agent for an oil, N-lauroyl-L-glutamic acid dibutylamide is known, and cosmetics containing this substance as a gelling agent have been reported (JP-A-51-19139). This gelling agent is known to gelatinize various oils. However, when the resulting gel composition is applied to the skin or hair, it does not necessarily give a superior feel and sometimes shows insufficient spreadability and the like.

Moreover, antiperspirant gel sticks containing 12-hydroxystearic acid and N-lauroylglutamic acid dibutylamide have been reported (U.S. Pat. No. 5,591,424 and JP-A-7-506833). However, these gel compositions, too, do not necessarily give a superior feel upon application to the skin or hair and sometimes show insufficient spreadability and the like.

As a different gelling agent for an oil, N-2-ethylhexanoyl-L-glutamic acid dibutylamide is known (JP-A-2002-316971), and cosmetics containing this substance as a gelling agent has been reported. While this gelling agent is known to gelatinize various oils, when the resulting gel composition is applied to the skin or hair, it does not necessarily give a superior feel and sometimes shows insufficient spreadability and the like.

SUMMARY OF THE INVENTION

It is therefore an object of the present invention to provide a gelling agent for an oil. To be specific, it is an object of the present invention to provide a gelling agent showing superior gel formability on an oil. It is also an object of the present invention to provide a gelling agent capable of producing a gel composition superior in spreadability upon application to the skin. Another object of the present invention is to provide a gel composition comprising a gelling agent having the above-mentioned characteristics and an oil, which is superior in spreadability upon application to the skin, hair and the like.

The present inventors have conducted intensive studies in an attempt to achieve the above-mentioned objects, and found that particular acidic amino acid derivatives are extremely superior as gelling agents for an oil, and a gel composition prepared from these acidic amino acid derivatives and oil is superior in gel strength and spreadability upon application to the skin or hair. In addition, they have found that the obtained gel composition has sufficient strength that allows use as a cosmetic, and even when it is formed into a stick form and the like, application to the skin or hair is easy. The present invention is predicated on the above-mentioned findings.

Accordingly, the present invention provides a gelling agent for an oil, which comprises at least one compound (A) represented by the following formula (A):

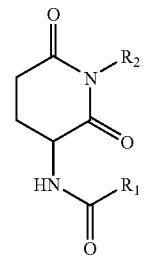

(A)

wherein $R_1$ is a straight chain or branched chain, saturated or unsaturated hydrocarbon group having 7 to 17 carbon atoms, and $R_2$ is a straight chain or branched chain, saturated or unsaturated hydrocarbon group having 1 to 26 carbon atoms, and at least one compound (B) represented by the following formula (B):

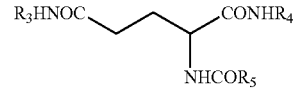

(B)

wherein $R_3$ and $R_4$ are each independently a straight chain or branched chain, saturated or unsaturated hydrocarbon group having 1 to 26 carbon atoms, and $R_5$ is a straight chain or branched chain, saturated or unsaturated hydrocarbon group having 7 to 17 carbon atoms.

In a different aspect of the invention, a gel composition comprising gelling agent (a) for an oil, which contains the above-mentioned compound (A) and compound (B), and at least one kind of oil (b) is provided by the present invention. In addition, the above-mentioned gel composition further containing at least one antiperspirant active ingredient (c) is provided. According to the present invention, moreover, a cosmetic comprising the above-mentioned gel composition is provided. This cosmetic may be preferably formed into a stick.

Using the gelling agent of the present invention for gelatinizing oil, a gel composition having a high gel strength and superior spreadability can be produced.

DETAILED DESCRIPTION OF THE INVENTION

Embodiments of the present invention are explained in the following additional description. As for compound (A), in the formula (A), $R_1$ is a straight chain or branched chain, saturated or unsaturated hydrocarbon group having 7 to 17 carbon atoms, and $R_2$ is a straight chain or branched chain, saturated or unsaturated hydrocarbon group having 1 to 26 carbon atoms. While the hydrocarbon group for $R_1$ may be a hydrocarbon group containing an unsaturated bond, a saturated hydrocarbon group is more preferable because preservation stability becomes high. For facilitated production, it is preferably a straight chain or branched chain alkyl group having 7 to 15 carbon atoms, more preferably 7 to 11 carbon atoms. While the hydrocarbon group for $R_2$ may be a hydrocarbon group containing an unsaturated bond, a saturated hydrocarbon group is more preferable because preservation stability becomes high. For facilitated production, it is preferably a straight chain or branched chain alkyl group having 1 to 10 carbon atoms, more preferably 2 to 6 carbon atoms, still more preferably 3 to 5 carbon atoms. Most preferable $R_2$ is an n-butyl group.

In view of versatility and easy production, compound (A) is preferably N-butyl-2-(N'-octanoylamino)glutarimide, N-butyl-2-(N'-2-ethylhexanoylamino)glutarimide, N-butyl-2-(N'-decanoylamino)glutarimide, N-butyl-2-(N'-lauroylamino)glutarimide, N-butyl-2-(N'-myristoylamino)glutarimide, N-butyl-2-(N'-palmitoylamino)glutarimide and the like. N-butyl-2-(N'-2-ethylhexanoylamino)glutarimide, N-butyl-2-(N'-decanoylamino)glutarimide and N-butyl-2-(N'-lauroylamino)glutarimide are particularly preferable.

As for compound (B), in the formula (B), $R_3$ and $R_4$ are each independently a straight chain or branched chain, saturated or unsaturated hydrocarbon group having 1 to 26 carbon atoms, and $R_5$ is a straight chain or branched chain, saturated or unsaturated hydrocarbon group having 7 to 17 carbon atoms. While the hydrocarbon group for $R_3$ or $R_4$ may be a hydrocarbon group containing an unsaturated bond, a saturated hydrocarbon group is more preferable because preservation stability becomes high. For facilitated production, it is preferably a straight chain or branched chain alkyl group having 1 to 10 carbon atoms, more preferably 2 to 6 carbon atoms, still more preferably 3 to 5 carbon atoms. Most preferable, one of $R_3$ and $R_4$ is an n-butyl group. While $R_5$ may be a hydrocarbon group containing an unsaturated bond, a saturated hydrocarbon group is more preferable. For facilitated production, it is preferably a straight chain or branched chain alkyl group having 7 to 15 carbon atoms, more preferably 7 to 11 carbon atoms.

In view of versatility and easy production, compound (B) is preferably N-octanoyl-L-glutamic acid dibutylamide, N-2-ethylhexanoyl-L-glutamic acid dibutylamide, N-decanoyl-L-glutamic acid dibutylamide, N-lauroyl-L-glutamic acid dibutylamide, N-myristoyl-L-glutamic acid dibutylamide, N-palmitoyl-L-glutamic acid dibutylamide and the like. N-2-ethylhexanoyl-glutamic acid dibutylamide and N-lauroyl-glutamic acid dibutylamide are particularly preferable.

Compound (A) is obtained by, for example, reacting N-acylglutamic acid-γ-methyl ester with alkylamine to give γ-alkylamide, and subjecting the resulting product to a heating dehydration condensation.

Compound (B) can be produced by, for example, reacting a long chain fatty acid halide with L-glutamic acid by Schotten Baumann's reaction in the presence of a basic catalyst to give N-acylated glutamic acid, and reacting the resulting product with an amine derivative such as alkylamine and the like with heating in the presence of an acid catalyst or without catalyst. Alternatively, compound (B) can be produced by reacting glutamic acid and an amine derivative such as alkylamine and the like in the presence of an acid catalyst or without catalyst to give glutamic acid amide, which is N-acylated with an acylating agent such as fatty acid halide and the like. In addition, commercially available products (e.g., N-lauroyl-L-glutamic acid dibutylamide, GP-1, manufactured by Ajinomoto Co., Inc.) can be used.

As compound (A) in the present invention, one kind of compound selected from the compounds represented by the formula (A) may be used, and two or more kinds of compounds selected from the compounds represented by the formula (A) may be used in combination.

As compound (B) in the present invention, one kind of compound selected from the compounds represented by the formula (B) may be used, and two or more kinds of compounds selected from the compounds represented by the formula (B) may be used in combination.

The content ratio of compound (A) and compound (B) in the gelling agent of the present invention is free of any particular limitation as long as they, in combination, can gelatinize oil. The lower limit of the content of compound (A) relative to 100 parts by weight of compound (B) is generally not less than 0.1 part by weight. When it is less than 0.1 part by weight, the spreadability of the obtained gel composition tends to become inferior upon application to the skin or hair. To achieve a clear effect and practical benefit, it is preferably not less than 0.5 part by weight, more preferably not less than 1 part by weight, still more preferably not less than 2 parts by weight, yet more preferably not less than 3 parts by weight, further more preferably not less than 5 parts by weight, especially preferably not less than 7 parts by weight, and particularly preferably not less than 9 parts by weight. The upper limit of the content of compound (A) relative to 100 parts by weight of compound (B) is generally not more than 50 parts by weight. When it is more than 50 parts by weight, the gel strength of the obtained gel composition tends to become poor. To achieve a clear effect and practical benefit, it is preferably not more than 30 parts by weight, more preferably not more than 25 parts by weight, still more preferably not more than 20 parts by weight, yet more preferably not more than 15 parts by weight, and particularly preferably not more than 10 parts by weight.

In the gel composition of the present invention, the amount of the gelling agent (a) containing compound (A) and compound (B) to be used is free of any particular limitation as long as it gelatinizes oil. Generally, 0.1–15 parts by weight is used relative to 100 parts by weight of the oil to be gelatinized. When it is less than 0.1 part by weight, sufficient gel strength may not be afforded, and when it is more than 15 parts by weight, the gelling agent (a) cannot be dissolved in oil, and the appearance of the obtained gelatinized oil may be impaired. To achieve a clear effect and practical benefit, it is preferably 0.5–10 parts by weight, more preferably 1–10 parts by weight, particularly preferably 2–10 parts by weight.

The oil to be used for the gel composition of the present invention is free of any particular limitation as long as it can sufficiently dissolve the above-mentioned gelling agent by heating, and form a gel when cooled to room temperature. Specific examples thereof include silicone oils; higher alcohols such as cetyl alcohol, isostearyl alcohol, lauryl alcohol, hexadecyl alcohol, octyldodecanol and the like; fatty acids such as isostearic acid, undecylenic acid, oleic acid and the like; polyhydric alcohols such as glycerol, sorbitol, ethylene glycol, propylene glycol, polyethylene glycol and the like; esters such as myristyl myristate, hexyl laurate, decyl oleate, isopropyl myristate, hexyldecyl dimethyloctanoate, glyceryl monostearate, diethyl phthalate, ethylene glycol monostearate and octyl oxystearate and the like; hydrocarbons such as n-tridecane, liquid paraffin, petrolatum, squalane and the like; waxes such as lanolin, reduced lanolin, carnauba wax and the like; fats and oils such as mink oil, cacao oil, coconut oil, palm seed oil, camellia oil, sesame oil, castor oil, olive oil and the like; ethylene/α-olefin co-ligomers and the like.

Examples of silicone oils include those selected from the group consisting of methylpolysiloxane, highly polymerized methylpolysiloxane, ether-modified silicones such as polyoxyethylene/methylpolysiloxane copolymer, polyoxypropylene/methylpolysiloxane copolymer, poly(oxyethylene or oxypropylene)/methylpolysiloxane copolymer and the like, stearoxymethylpolysiloxane, stearoxytrimethylsilane, methyl hydrogen polysiloxane, octamethylpolysiloxane, decamethylpolysiloxane, cyclic silicones such as decamethylcyclopentasiloxane, octamethylcyclotetrasiloxane, tetrahydrotetramethylcyclotetrasiloxane, methylcyclopolysiloxane, cyclopentasiloxane, dodecamethylcyclohexasiloxane and the like; methylphenylpolysiloxane, trimethylsiloxy silicate, amino-modified silicones such as aminoethylaminopropylsiloxane/dimethylsiloxane copolymer and the like, silanol-modified polysiloxanes, alkoxy-modified polysiloxanes, aliphatic acid-modified polysiloxanes, fluorine-modified polysiloxanes, epoxy-modified polysiloxanes, alkoxy-modified polysiloxane perfluoropolyethers, polyvinyl acetate dimethyl polysiloxane, and mixtures thereof.

The oil may be a mixture of one or more kinds of oils.

An oil is generally used in a proportion of 10–99.9 wt % of the total weight of a gel composition. When the content of the oil is less than 10 wt %, or when it is more than 99.9 wt %, sufficient gel strength may not be afforded.

The gel composition of the present invention can remarkably sustain the antiperspirant effect particularly when an antiperspirant active ingredient (c) is further contained in the gel composition. In the present specification, by the "antiperspirant active ingredient" is basically meant a component that suppresses perspiration by astringing the skin; however, this term should be interpreted in the widest sense and is free of any limitation in the linguistic interpretation. The kind of antiperspirant active ingredient is not particularly limited, and two or more kinds of antiperspirant active ingredients may be used in combination. As the antiperspirant active ingredient, for example, chlorohydroxy aluminum, aluminum chloride, allantoin chlorohydroxy aluminum, aluminum sulfate, zinc oxide, zinc PCA, zinc paraphenolsulfonate or a zirconium aluminum complex produced by reacting zirconyl chloride with aluminum hydroxide and aluminum chlorohydroxide, and the like can be mentioned. An antiperspirant active ingredient is used in a proportion of generally 1–60 wt % of the total weight of the gel composition. When the antiperspirant active ingredient is less than 1 wt %, the antiperspirant function tends to be insufficient, and when it is greater than 60 wt %, the irritation to the skin or hair may become stronger. To achieve a clear effect and practical benefit, it is preferably contained in 5–35 wt %. In addition, the antiperspirant active ingredient may be added in the form of a solution or fine particles. When it is used in the form of fine particles, the particle size of a substance to be the antiperspirant active ingredient is generally 1–100 microns, and preferably 1–50 microns to afford high bulk density.

When the above-mentioned antiperspirant active ingredient (c) is added to the gel composition of the present invention, the addition of various chelating agents (d) to the gel composition is more effective for sustaining its effectiveness and suppressing discoloration and occurrence of odor. While the kind of chelating agent is not particularly limited, a chelating agent selected from the group consisting of triethylenetetramine, 1,1,1-trifluoro-3,2'-thenoylacetone, thioglycolic acid, tartaric acid, succinic acid, 8-quinolinol, pyridine-2,6-dicarboxylic acid, pyridine, 1,10-phenanthroline, lactic acid, 8-hydroxyquinoline-5-sulfonic acid, glycine, 2,2'-pyridylethylenediamine, Xylenol Orange, 5-sulfosalicylic acid, salicylic acid, pyrocatechol-3,5-disulfonate, 4,5-dihydroxybenzene-1,3-disulfonic acid, 1,2-diaminocyelohexane-N,N,N',N'-tetraacetic acid, citric acid, oxalate, nitrilotriacetic acid, ethylenediamine-N,N,N',N'-tetraacetic acid, acetylacetone and salts thereof, and a mixture thereof and the like can be mentioned.

The production method of the gel composition of the present invention is not particularly limited. For example, the above-mentioned gelling agent (a), oil (b), and, where necessary, other components, an antiperspirant active ingredient (c), and further, a chelating agent (d) and the like can be mixed and heated to generally 50–180° C. with stirring. Thereafter, the mixture is cooled to give the object gel composition.

The gelling agent (a) of the present invention may further contain one or more kinds of gelling agents for an oil. The gelling agent for an oil can be, for example, polyamide resin, 12-hydroxystearic acid, sodium stearate, dibenzylidene-D-sorbitol and the like.

The use of the cosmetic of the present invention is not particularly limited. For example, the cosmetic can be in the form of gel cosmetics, pack cosmetics, granule cosmetics, stick cosmetics and the like. The cosmetic of the present invention can be prepared as a uniform composition by preparing the above-mentioned gel composition, adding and blending one or more kinds of additives recited in the following as necessary. The production step thereof is not particularly limited, and general means of mixing, stirring, kneading and the like available to those of ordinary skill in the art can be used appropriately. The cosmetic of the present invention is characterized in that the active ingredient can be sustainably retained in a gel form as compared to cosmetics in a liquid form.

In addition, the cosmetic of the present invention can contain other ingredients, such as surfactants, various additives and various fine particles, desirably within a range such that the desirable properties of the present invention are not unduly obviated. As the surfactant, any of anionic surfactants, nonionic surfactants, cationic surfactants and ampholytic surfactants can be used. As the anionic surfactants, for example, N-long chain acyl amino acid salts such as N-long chain acyl acidic amino acid salts, N-long chain acyl neutral amino acid salts and the like, N-long chain aliphatic acid acyl-N-methyltaurine salts, alkyl sulfates and alkylene oxide adducts thereof, aliphatic acid amide ether sulfates, metal salts and weak base salts of aliphatic acids, sulfosuccinic acid type surfactants, alkylphosphates and alkylene oxide adducts thereof, alkyl ether carboxylic acids and the like can be mentioned. As the nonionic surfactants, for example, ether type surfactants such as glyceryl ethers, alkylene oxide adducts thereof and the like, ester type surfactants such as glyceryl esters, alkylene oxide adducts thereof and the like, ether ester type surfactants such as sorbitan esters, alkylene oxide adducts thereof and the like, ester type surfactants such as polyoxyalkylene aliphatic acid esters, glyceryl esters, aliphatic acid polyglyceryl esters, sorbitan esters, sucrose fatty acid esters and the like, alkyl glucosides, nitrogen-containing nonionic surfactants such as hydrogenated castor oil pyroglutamic acid diesters and ethylene oxide adducts thereof, fatty acid alkanolamides and the like, and the like can be mentioned. As the cationic surfactants, for example, aliphatic amine salts such as alkylammonium chlorides, dialkylammonium chlorides and the like, quaternary ammonium salts thereof, aromatic quaternary ammonium salts such as benzalkonium salts and the like, fatty acid acyl arginine esters and the like can be mentioned. As the ampholytic surfactants, for example, betaine type surfactants such as carboxybetaine and the like, aminocarboxylic acid type surfactants, imidazoline type surfactants and the like can be mentioned.

The various additives can be, for example, amino acids such as glycine, alanine, serine, treonine, arginine, glutamic acid, aspartic acid, leucine, valine and the like; polyhydric alcohols such as glycerol, ethylene glycol, 1,3-butylene glycol, propylene glycol, isoprene glycol and the like; fatty acid alkylamides such as 2-ethylhexanoic acid butylamide and the like; water-soluble polymers such as polyamino acids including polyglutamic acid and polyaspartic acid and a salt thereof, polyethylene glycol, gum arabic, alginic acid salt, xanthane gum, hyaluronic acid, hyaluronic acid salt, chitin, chitosan, water-soluble chitin, carboxyvinyl polymer, carboxymethyl cellulose, hydroxyethyl cellulose, hydroxypropyltrimethyl ammonium chloride, poly(dimethylmethylene piperidium chloride), quaternary ammonium of polyvinylpyrrolidone derivative, cationized protein, collagen decomposition product and derivatives thereof, acylated protein, polyglycerol and the like; sugar alcohols such as mannitol and the like and alkylene oxide adducts thereof; lower alcohols such as ethanol, propanol and the like; antibacterial agents such as benzalkonium chloride, benzethonium chloride, halocarban, chlorhexidine hydrochloride and the like, and the like, as well as animal and plant extracts, nucleic acids, vitamins, enzymes, anti-inflammatory agents, preservatives, antioxidants, UV absorbers, pigments, dyes, oxidation dyes, organic and inorganic fine particles, pH-adjusters, pearling agents, wetting agents and the like.

The various fine particles can be, for example, resin fine particles such as nylon beads, silicone beads and the like, nylon powder, aliphatic acid metal salt soap, yellow iron oxide, red iron oxide, black iron oxide, chrome oxide, cobalt oxide, carbon black, ultramarine blue, Berlin blue, zinc oxide, titanium oxide, zirconium oxide, silicon oxide, aluminum oxide, cerium oxide, mica-titanium, boron nitride, barium sulfate, calcium carbonate, magnesium carbonate, aluminum silicate, magnesium silicate, silicon carbide, dyes, lakes, sericite, mica, talc, kaolin, tabular barium sulfate, butterfly-shaped barium sulfate, microparticle titanium oxide, microparticle zinc oxide, microparticle iron oxide, acylamino acids such as acyllysine, acylglutamic acid, acyllarginine, acylglycine etc., and the like. As the fine particles, those subjected to a surface treatment such as silicone treatment, a fluoro-compound treatment, a silane coupling agent treatment, a silanized organic titanate treatment, an acylated lysine treatment, an aliphatic acid treatment, a metallic soap treatment, an oil treatment, an amino acid treatment and the like can be used.

EXAMPLES

The present invention is explained in detail by referring to Examples, which are not to be construed as limitative.

Production Example 1

Synthesis of
N-butyl-2-(N'-lauroylamino)glutarimide

N-Lauroylglutamic acid-γ-methyl ester (6.8 g, 0.02 mol) was dissolved in toluene (10 g), and butylamine (9 g, 0.12 mol) was added thereto. The mixture was heated to 90° C. for 4 hr. Water was added, and the mixture was neutralized with sulfuric acid and extracted. The solvent was evaporated to give γ-butylamide derivative. This product (6 g) was taken and reacted under nitrogen at 160° C. for 6.5 hr. Ethyl acetate and aqueous NaOH solution were added, and the mixture was extracted. The organic layer was dried over $Na_2SO_4$ and $MgSO_4$. The solvent was evaporated to give the reaction product. This reaction product was purified by PTLC (ethyl acetate:hexane=1:2) to give the object product, N-butyl-2-(N'-lauroylamino)glutarimide.

Example 1

Production of Gel Composition

N-Butyl-2-(N'-lauroylamino)glutarimide (0.0005 part by weight) as compound (A) and N-lauroyl-L-glutamic acid dibutylamide (0.1995 part by weight) as compound (B) were added to n-tridecane (20 parts by weight) as oil (b), and the mixture was dissolved by heating in an oil bath at 150° C. The mixture was allowed to cool to 23° C. for 15 hr to give a gel composition.

Examples 2–7

Comparative Example 1

In the same manner as in Example 1 except that compound (A), compound (B) and oil (b) were used in the amounts shown in Table 1, respective gel compositions were obtained.

[Evaluation of Gel Formability]

The gel strength of the gel compositions of Examples and Comparative Example was measured with a rheo meter (FUDOH RHEO METER NRM-2010-J-CW). The adapter was for plume and viscoelasticity, 10φ, and sample stage velocity was 6 cm/min. The gel formability results are shown in Table 1. A gel strength at not less than 90 $g/cm^2$ was evaluated to be ⊙, 70–90 $g/cm^2$ was evaluated to be Δ, and less than 70 $g/cm^2$ was evaluated to be X.

[Evaluation of Spreadability]

The spreadability upon application of the gel compositions of Examples and Comparative Example to the skin was evaluated based on the following evaluation standard by 5 expert panelists.
  5: highly superior in spreadability
  4: superior in spreadability
  3: average
  2: inferior in spreadability
  1: very inferior in spreadability
The spreadability results are shown in Table 1. An average evaluation result of not less than 4.5 was evaluated to be ⊙, 3.5–4.4 was evaluated to be ○, 2.5–3.4 was evaluated to be Δ, and not more than 2.4 was evaluated to be X.

TABLE 1

|  | Comparative Example 1 | Example 1 | Example 2 | Example 3 | Example 4 | Example 5 | Example 6 | Example 7 |
|---|---|---|---|---|---|---|---|---|
| (a) gelling agent | | | | | | | | |
| A  N-butyl-2-(N'-lauroylamino)-glutarimide | 0 | 0.0005 | 0.0015 | 0.003 | 0.005 | 0.01 | 0.02 | 0.09 |
| B  lauroyl-L-glutamic acid dibutylamide* | 0.2 | 0.1995 | 0.1985 | 0.197 | 0.195 | 0.19 | 0.2 | 0.2 |
| (b) oil | | | | | | | | |
| n-tridecane | 20 | 20 | 20 | 20 | 20 | 20 | 20 | 20 |
| results of evaluation | | | | | | | | |
| gel formability | ○ | ○ | ○ | ○ | ○ | ○ | ○ | △ |
| spreadability | X | △ | ○ | ○ | ⊚ | ⊚ | ⊚ | ⊚ |
| A ratio (relative to B100) | 0.0 | 0.3 | 0.8 | 1.5 | 2.6 | 5.3 | 10.0 | 45.0 |

*GP-1 (Ajinomoto Co., Ltd.)

Preparation Example 1

Production of Antiperspirant Gel Stick

| 1) | N-butyl-2-(N'-lauroylamino) glutarimide | 0.02 g |
|---|---|---|
| 2) | N-lauroyl-L-glutamic acid dibutylamide | 1.0 g |
| 3) | N-2-ethylhexanoyl-L-glutamic acid dibutylamide | 1.0 g |
| 4) | 2-ethylhexanoic acid butylamide | 0.01 g |
| 5) | 12-hydroxystearic acid | 7.0 g |
| 6) | octyldodecanol | 14.0 g |
| 7) | CYCLOMETHICONE D-5 (SH245, Dow Corning Toray Corporation) | 48.0 g |
| 8) | Aluminum Zirconium Tetrachlorohydrex Glycine (Westchlor ZR 30B DM CP-5, WESTWOOD CHEMCAL Corporation) | 26.0 g |

The above-mentioned items 1)–7) were dissolved at 130° C., and the above-mentioned item 8) was added. The mixture was allowed to cool with stirring to give an antiperspirant gel stick. This product had sufficient strength and showed fine spreadability upon application to the skin.

The gelling agent for an oil of the present invention affords a gel composition having high gel strength and superior spreadability, and can be used for, for example, cosmetics having various forms of gel cosmetics, pack cosmetics, stick cosmetics and the like. Furthermore, it is also useful as an industrial gel such as ink, gear oils, asphalt and the like or a highly viscous base.

This application is based on Application No. 2003-382921 filed in Japan, the contents of which are incorporated hereinto by reference.

What is claimed is:

1. A gelling agent for an oil, which comprises at least one compound (A) selected from the group consisting of N-butyl-2-(N'-lauroylamino)glutarimide and N-butyl-2-(N'-2-ethylhexanoylamino)glutarimide, and
   at least one compound (B) selected from the group consisting of N-lauroyl-L-glutamic acid dibutylamide and N-2-ethylhexanoyl-L-glutamic acid dibutylamide.

2. The gelling agent of claim 1 wherein the content of compound (A) is not less than 0.1 part by weight and not more than 50 parts by weight relative to 100 parts by weight of compound (B).

3. The gelling agent of claim 1 wherein the content of compound (A) is not less than 0.5 part by weight and not more than 50 parts by weight relative to 100 parts by weight of compound (B).

4. The gelling agent of claim 1 wherein the content of compound (A) is not less than 1 part by weight and not more than 50 parts by weight relative to 100 parts by weight of compound (B).

5. The gelling agent of claim 1 wherein the content of compound (A) is not less than 2 parts by weight and not more than 50 parts by weight relative to 100 parts by weight of compound (B).

6. The gelling agent of claim 1 wherein the content of compound (A) is not less than 3 parts by weight and not more than 50 parts by weight relative to 100 parts by weight of compound (B).

7. The gelling agent of claim 1 wherein the content of compound (A) is not less than 5 parts by weight and not more than 50 parts by weight relative to 100 parts by weight of compound (B).

8. The gelling agent of claim 1 wherein the content of compound (A) is not less than 7 parts by weight and not more than 50 parts by weight relative to 100 parts by weight of compound (B).

9. The gelling agent of claim 1 wherein the content of compound (A) is not less than 9 parts by weight and not more than 50 parts by weight relative to 100 parts by weight of compound (B).

10. A gel composition comprising (a) the gelling agent of claim 1 and (b) at least one oil.

11. The gel composition of claim 10 further comprising (c) at least one antiperspirant active ingredient.

12. A cosmetic comprising the gel composition of claim 10.

13. A cosmetic comprising the gel composition of claim 11.

14. The gelling agent of claim 1, wherein compound (A) is N-butyl-2-(N'-lauroylamino)glutarimide and compound (B) is N-lauroyl-L-glutamic acid dibutylamide.

15. The gelling agent of claim 1, wherein compound (A) is N-butyl-2-(N'-lauroylamino)glutarimide and compound (B) is N-2-ethylhexanoyl-L-glutamic acid dibutylamide.

16. The gelling agent of claim 1, wherein compound (A) is N-butyl-2-(N'-2-ethylhexanoylamino)glutarimide and compound (B) is N-lauroyl-L-glutamic acid dibutylamide.

17. The gelling agent of claim 1, wherein compound (A) is N-butyl-2-(N'-2-ethylhexanoylamino)glutarimide and compound (B) is N-2-ethylhexanoyl-L-glutamic acid dibutylamide.

18. A method of improving the spreadability of a gel composition comprising an oil for application to the skin or the hair, comprising:
  (i) at least one compound (A) selected from the group consisting of N-butyl-2-(N'-lauroylamino)glutarimide and N-butyl-2-(N'-2-ethylhexanoylamino)glutarimide:
  (ii) at least one compound (B) selected from the group consisting of N-lauroyl-L-glutamic acid dibutylamide and N-2-ethylhexanoyl-L-glutamic acid dibutylamide; and
  (iii) at least one oil to form a gel composition,
  wherein the addition of compound (A) improves the spreadability of the gel compisition.

19. A method of improving the spreadability of a gel composition for application to the skin or the hair of claim 18, wherein compound (A) is N-butyl-2-(N'-lauroylamino) glutarimide and compound (B) is N-lauroyl-L-glutamic acid dibutylamide.

20. A method of improving the spreadability of a gel composition for application to the skin or the hair of claim 18, wherein compound (A) is N-butyl-2-(N'-lauroylamino) glutarimide and compound (B) is N-2-ethylhexanoyl-L-glutamic acid dibutylamide.

21. A method of improving the spreadability of a gel composition for application to the skin or the hair of claim 18, wherein compound (A) is N-butyl-2-(N'-2-ethylhexanoylamino)glutarimide and compound (B) is N-lauroyl-L-glutamic acid dibutylamide.

22. A method of improving the spreadability of a gel composition for application to the skin or the hair of claim 18, wherein compound (A) is N-butyl-2-(N'-2-ethylhexanoylamino)glutarimide and compound (B) is N-2-ethylhexanoyl-L-glutamic acid dibutylamide.

23. The gel composition of claim 11 further comprising (d) at least one chelating agent.

* * * * *